United States Patent
Gande et al.

(10) Patent No.: US 12,427,104 B1
(45) Date of Patent: Sep. 30, 2025

(54) INJECTABLE CARBOPLATIN FORMULATIONS

(71) Applicant: Ingenus Pharmaceuticals, LLC, Orlando, FL (US)

(72) Inventors: Mukteeshwar Gande, Monroe, NJ (US); Praveen Reddy Billa, Flanders, NJ (US); Venkata S. Varanasi, Fogelsville, PA (US); Samir Chimanlal Mehta, Morrisville, NC (US)

(73) Assignee: Ingenus Pharmaceuticals, LLC, Orlando, FL (US)

( * ) Notice: Subject to any disclaimer, the term of this patent is extended or adjusted under 35 U.S.C. 154(b) by 0 days.

(21) Appl. No.: 19/097,811

(22) Filed: Apr. 1, 2025

(51) Int. Cl.
*A61K 9/00* (2006.01)
*A61K 31/555* (2006.01)
*A61K 47/02* (2006.01)

(52) U.S. Cl.
CPC .......... *A61K 9/0019* (2013.01); *A61K 31/555* (2013.01); *A61K 47/02* (2013.01)

(58) Field of Classification Search
CPC ..... A61K 9/0019; A61K 31/555; A61K 47/02
See application file for complete search history.

(56) References Cited

U.S. PATENT DOCUMENTS

| | | | |
|---|---|---|---|
| 5,104,896 A | 4/1992 | Nijkerk et al. | |
| 5,455,270 A | 10/1995 | Kaplan et al. | |
| 6,234,333 B1 | 5/2001 | Federighi et al. | |
| 6,589,988 B1 | 7/2003 | Kysilka et al. | |
| 9,937,187 B2 | 4/2018 | Bilodeau et al. | |
| 2006/0216360 A1* | 9/2006 | Kumar et al. ........ | A61K 31/555 424/649 |
| 2010/0114058 A1 | 5/2010 | Weitzel et al. | |
| 2023/0140586 A1 | 5/2023 | Kuma et al. | |

FOREIGN PATENT DOCUMENTS

| | | |
|---|---|---|
| EP | 0334551 A1 | 3/1989 |
| WO | 9520956 A1 | 8/1995 |

OTHER PUBLICATIONS

Tiwari et al. (Study of the Excess Cost Associated with Drug Wastage Due to Limited Vial Size Options of the Intravenous Drugs for anti-cancer treatment, Among Patients Receiving Such treatment at Tata Memorial Hospital, Asian Pac J Cancer Care, Sep. 2024 (Year: 2024).*
Prescribing Information of Carboplatin Injection (Hospira, Revised: Apr. 2018) (Year: 2018).*
Bristol-Myers Squibb Company, Paraplatin (carboplatin) Injection, Rx only, Label, 21 pp, Jul. 2010.
Woloschuk et al., Carboplatin: a New Cisplatin Analog, Investigational Drug Information, Drug Intelligence and Clinical Pharmacy, Nov. 1988, vol. 22, pp. 843-849.
Duffull et al., Clinical Pharmacokinetics and Dose Optimisation of Carboplatin, Drug Disposition, Clinical Pharmacokinetics, Sep. 1997, vol. 33, pp. 161-183.
Liran et al., A real-world analysis of cancer drug wastage due to oversized vials, Journal of the American Pharmacists Association, Elsevier Publication, vol. 58, Issue 6, 2018, pp. 643-646.
Goenka et al., Cost Analysis Of Drug Wastage In An Oncology Day Care, International Journal of Life Sciences, Biotechnology and Pharma Research, vol. 12, No. 4, Oct.-Dec. 2023, pp. 1331-1335.
Chatelut et al., Dose banding as an alternative to body surface area-based dosing of chemotherapeutic agents, British Journal of Cancer, 2012, vol. 107, No. 7, pp. 1100-1106.
Kaestner et al., A National Survey Investigating UK Prescribers' Opinions on Chemotherapy Dosing and 'Dose- Banding', The Royal College of Radiologists, Elsevier Publication, Clinical Oncology, 2009, vol. 21, pp. 320-328.
Hess et al., Drug wastage and costs to the healthcare system in the care of patients with non-small cell lung cancer in the United States, Journal of Medical Economics, 2018, vol. 21., No. 8, pp. 755-761.
D'Souza et al., Financial audit of wastage of anticancer drugs: Pilot study from tertiary care center in India, Indian Journal of Cancer, vol. 56, issue 2, Apr.-Jun. 2019, pp. 146-150.
Ariana Pelosci, Generic Drug Shortage is Creating Treatment Barriers Across Cancer Space, CancerNetwork, Jul. 27, 2023, 8 pp.
Fulsoundar et al., Quantifying Drug Wastage and Economic Loss of Chemotherapy Drugs at an Adult Oncology Care of a Tertiary Care Public Hospital in India, Cureus, vol. 15, No. 11, 2023, 8 pp.
Hatswell et al., The Cost of Costing Treatments Incorrectly: Errors in the Application of Drug Prices in Economic Evaluation Due to Failing to Account for the Distribution of Patient Weight, ScienceDirect, vol. 19, 2016, pp. 1055-1058.
Matsuo et al., Estimating the effect of optimizing anticancer drug vials on medical costs in Japan based on the data from a cancer hospital, BMC Health Services Research, vol. 20:1017, 2020, 7 pp.

* cited by examiner

*Primary Examiner* — Robert A Wax
*Assistant Examiner* — John Seungjai Kwon
(74) *Attorney, Agent, or Firm* — The Belles Group, P.C.

(57) ABSTRACT

Described herein are injectable carboplatin formulations, comprising: about 10 mg/mL of carboplatin; and a pharmaceutically acceptable vehicle; wherein the formulation has a pH of from about 5 to about 7; wherein the formulation has a dissolved oxygen level of not less than about 28 ppm; wherein the formulation is filled in a vial at a fill volume of from about 1 mL to about 70 mL in a vial having a capacity of from about 1 mL to about 100 mL; wherein the vial has head space ranging from about 20% to about 82%; and wherein the headspace comprises oxygen gas in an amount effective to maintain a 1,1-cyclobutanedicarboxylic acid level of not more than 1.0%, based on the weight of carboplatin, and a total degradation impurity level at not more than 2.5%, based on the weight of carboplatin, when stored at room temperature for 24 months.

10 Claims, No Drawings

INJECTABLE CARBOPLATIN FORMULATIONS

FIELD OF THE DISCLOSURE

The present disclosure relates to stable injectable pharmaceutical formulations comprising carboplatin, or a pharmaceutically acceptable derivative thereof; and a pharmaceutically acceptable vehicle. Specifically, the disclosure pertains to the development of injectable carboplatin formulations which are filled in glass vials with optimized packaging configurations designed to minimize drug wastage, enhance patient and healthcare provider compliance while maintaining the standard strength, stability, and therapeutic efficacy. The disclosure further describes processes for preparing the formulations and methods for treating patients suffering with cancer through the administration of the formulations described herein. The present disclosure also describes environmentally friendly carboplatin manufacturing, which reduces the overall wastage of platinum.

BACKGROUND

Carboplatin is a platinum co-ordination compound, having the chemical name cis diamine(cyclobutane-1,1-dicarboxylate-O,O')platinum(II). The key raw material for carboplatin manufacture is platinum, which is a precious and rare earth metal, present to an extent of 0.005 parts per million (ppm) in the Earth's crust. It is extremely important to utilize every gram of platinum effectively as it would need almost eleven or twelve tons of platinum ore and extensive processing to obtain one troy ounce (31.103 grams) of pure platinum. The processing of ore to platinum is extremely labour intensive and can take anywhere between eight weeks to six months. The production of platinum involves complex mining and refining processes, including ore extraction, smelting, and multiple purification steps to remove impurities and obtain pure platinum. There are several steps to convert ore to platinum like excavation, crushing, extraction, refining. Excavation can result in destruction of forests; loss of habitats and biodiversity; soil erosion and overburden, crippling effects on workers, ecological diseases—e.g., silicosis, tuberculosis etc. The subsequent steps result in: a) release of toxic elements; b) increase of SOx levels; c) higher suspended particulate matter; and d) adverse health impact on the work force with higher incidents of respiratory disorders like platinum-induced asthma, skin rashes, allergies etc. Due to the scarcity and high cost of platinum, optimizing its utilization in pharmaceutical formulations is critical.

Carboplatin is an important chemotherapy drug widely used in the United States and globally. It has been pivotal in the treatment of a wide array of cancers. It is available commercially in the form of a lyophilized powder and pre-concentrate aqueous solution (10 mg/mL) under the brand name Paraplatin® from Bristol-Myers Squibb. It is typically provided in specific packaging configurations, with a limited range of strengths and fill volumes. These include formulations with a strength of 10 mg/mL carboplatin in multi-dose vials, packaged as 50 mg/5 mL, 150 mg/15 mL, 450 mg/45 mL and 600 mg/60 mL.

The recommended dose of Paraplatin® injection depends on patient-specific factors, particularly body surface area (BSA), area under the curve (AUC) and renal function. Dose modifications of carboplatin injection are based on hematologic parameters and renal function of the patient. The dose for carboplatin injection is calculated using the Calvert formula:

Dose (mg)=Target AUC×(GFR+25), where AUC (Area Under Curve) represents drug exposure and GFR (Glomerular Filtration Rate) is a measure of kidney function.

Doses are typically tailored to achieve optimal therapeutic outcomes while minimizing adverse effects. As carboplatin doses are individualized based on BSA and renal function, wastage often occurs when the commercially available vial sizes do not align with calculated patient-centric or specific therapeutic doses.

In particular, the currently marketed configurations pose significant challenges and lead to inefficiencies during clinical use, particularly for recommended dosages for certain clinical conditions (e.g., 360 mg/m$^2$, 300 mg/m$^2$, 250 mg/m$^2$, and 200 mg/m$^2$ of body surface area). For instance, a patient requiring a dosage of 300 mg/m$^2$ might require the use of multiple vials or the partial use of a vial. More specifically, a patient requiring 525 mg of carboplatin may need to use both a 450 mg vial and a 150 mg vial, leading to a considerable amount of leftover drug product. Also, in accordance with approved dosing regimens, Paraplatin® injection is administered as a single agent in patients with recurrent ovarian carcinoma at a dosage of 360 mg/m$^2$ IV on day 1 every 4 weeks; and in patients with advanced ovarian cancer, Paraplatin® injection is administered in combination with cyclophosphamide at a dosage of 300 mg/m$^2$ IV on day 1 every 4 weeks for 6 cycles. Smaller clinics and hospitals may not be able to use all the drug from a single vial on a single patient. Also, both single agent therapy and combination therapy are not to be repeated until the neutrophil count of the patient is at least 2,000 and the platelet count of the patient is at least 100,000. As such, many patients are not able to receive follow-up treatment within 14 days, which is the shelf life of a multidose vial after first use. Paraplatin® vials maintain microbial, chemical, and physical stability for up to 14 days at room temperature (25° C.) following multiple needle entries. This means that once the vial is partially used, unless there is another patient within 14 days, the contents of the vial will be discarded (i.e., wasted). Additionally, multiple needle entries into a single vial increase the risk of cross-contamination and errors in tracking multi-dose vial usage, further complicating safe administration.

There may also be compatibility issues between products supplied by various manufacturers. So, healthcare providers prefer not to mix products from different manufacturers.

The mismatch of variable doses, uncertainty with the availability of patient(s) and the stability of commercially available vials of specific packaging configuration results in leftover product that cannot be stored for extended periods of time or reused due to sterility concerns, leading to wastage of drug product.

Indeed, several studies have highlighted the problem of wastage of anticancer drugs that use existing commercial packaging. Hess et. al conducted a study to determine drug wastage and the cost to the healthcare system in caring for patients with non-small cell lung cancer in the United States; and concluded that about 4.52% of carboplatin was wasted. Goenka A et al. Int J Life Sci Biotechnol Pharma Res. 2024 February; 12(4):1331-35 reported that on an average about 8.5% of carboplatin was wasted in oncology units. Fulsoundar R et al. Cureus. 2023 November; 15(11): e49242 conducted a study for quantifying drug wastage and economic loss of chemotherapy drugs and concluded that the highest proportion of drug wastage was observed for carboplatin (2,525 mg/7,200 mg [or 35.06%]) among all anticancer drugs.

In addition, carboplatin being a cytotoxic drug, requires stringent handling and disposal protocols in hospital and nursing home settings to comply with regulatory and environmental safety standards. In many cases, the preparation of chemotherapy doses results in excess drug volume, which must be properly disposed of as hazardous medical waste. The disposal process involves specialized containment, neutralization, and waste management procedures to prevent environmental contamination and occupational exposure. This adds operational complexity and additional cost to healthcare facilities.

Further, in early 2023, FDA identified a shortage of carboplatin injection for the first time and the problem remains unresolved. All approved commercial pack sizes are not always available through all wholesalers which presents a challenge for clinics and hospitals to purchase the injection for patients. This is evident from the global sales data viz. in 2024, 66.73% of the 60 mL pack size was sold, 23.19% of the 45 mL pack size was sold, 6.63% of 15 mL pack size was sold and 3.45% of 5 mL pack size was sold. From this data, it is clear that the shortage of carboplatin injection is due—at least in part—to the low availability of appropriate suitable commercial pack sizes at all times.

The global shortage of carboplatin injection has significantly impacted cancer treatment protocols, forcing patients and healthcare providers to seek alternative therapies. These shortages have been attributed to disruptions in the pharmaceutical supply chain, manufacturing constraints, and increased demand. As a result, many patients are being prescribed substitute chemotherapy agents or combination therapies that may not offer the same efficacy in tumour response or may present a higher risk of adverse effects. The lack of availability of carboplatin has led to delays in treatment initiation, modifications to standard regimens; and, in some cases, the discontinuation of planned chemotherapy cycles. These challenges not only compromise patient outcomes but also place an increased financial burden on healthcare systems due to the higher costs associated with alternative drugs, additional monitoring, and potential hospitalizations caused by poorly tolerated alternate therapies.

The problem of wastage of carboplatin injection together with the global shortage of the drug needs to be addressed efficiently so that injectable carboplatin is made available for critically ill cancer patients in a timely manner. The shortage of carboplatin could be addressed by reducing its wastage.

Some researchers have suggested approaches to mitigate the problem of wastage. The approach of dose banding was suggested such as in Chatelut E et al. Br J Cancer. 2012 August; 107(7):1100-6. However, owing to lack of medical practitioners' faith regarding the safety of such an approach, this could not be implemented effectively. This further emphasizes the need for optimized formulations or delivery systems that minimize wastage of carboplatin injection while ensuring consistent drug availability.

While many researchers have attempted to address the problem of wastage of anticancer drugs, none have specifically addressed the problem by using packaging configurations and optimal fill volumes.

Apart from the problems of wastage and shortage of drug, another issue with administration of Paraplatin© injection is that it must be diluted to concentrations as low as 0.5 mg/mL with 5% dextrose in water (D5W) or 0.9% Sodium Chloride Injection, USP and then administered intravenously, over 15 minutes or more, to the patient. Generally, when the required therapeutic dose exceeds the amount contained in a single vial, multiple vials are opened and combined to match the prescribed dose before dilution and administration. Similarly, in the case of carboplatin, healthcare providers in hospitals and clinics must use multiple vials to achieve the calculated therapeutic dose, dilute the open vials, mix the contents of the vials with infusion fluid to get the desired concentration and then administer the drug as an infusion. This diluted Paraplatin® solution is stable for eight hours at room temperature and after eight hours the diluted solution must be discarded. During this process of dilution, which is performed by a healthcare provider, there are chances of dosing errors, drug spillage and contamination, potentially leading to improper dosing and an increased risk of patient harm. Therefore, reducing the number of vials required to deliver the therapeutic dose would be highly advantageous, as it would minimize dosing errors, reduce contamination risks, and ultimately enhance patient outcomes.

The foregoing not only creates economic inefficiencies because carboplatin is expensive, but it also contributes to logistical challenges for healthcare providers in clinical settings.

Accordingly, there is a need to develop vials with new packaging configurations containing injectable carboplatin formulations which will reduce the wastage of carboplatin and increase patient and healthcare provider compliance. The present inventors evaluated various options before selecting the inventive packaging configurations of the vial sizes having optimal fill volumes to address the issues of wastage of drug, shortage of drug and non-compliance of patient and healthcare providers. Embodiments of the present invention are designed to address the challenges faced due to administration of commercial packaging sizes of vials by introducing alternate packaging configurations of vials having optimized fill volumes of carboplatin injection. The formulations and methods of the present invention have the potential for wide applicability in oncology treatment settings, where carboplatin is a cornerstone therapy. By optimizing vial strengths and reducing wastage, the proposed formulations align with the needs of healthcare providers, patients, regulatory bodies, and environmentalists ensuring broad adoption and commercial benefit.

One of the challenges faced by the present inventors was to maintain the stability of the formulations in the proposed packaging sizes. Researchers have proposed certain approaches to maintain the stability of carboplatin formulations in the past. However, none of the proposed solutions use innovative packaging configurations and/or optimal fill volumes to address the issues. Certain embodiments of the present invention are designed to meet these, and other, ends.

SUMMARY

Some embodiments of the present invention provide a formulation that: a) ensures efficient use of carboplatin; b) minimizes wastage; c) maintains therapeutic efficacy; and/or d) remains stable for extended periods of time at room temperature. By carefully selecting optimal fill volumes and packaging configurations, embodiments of the present invention aim to enhance resource efficiency and reduce unnecessary platinum loss, improve patient and practitioner compliance, and ensure cost-effectiveness and sustainability in oncology treatments. The present inventors conducted numerous formulation studies to arrive at the packaging configurations of glass vials which are filled with optimal fill volumes of carboplatin formulations with predefined quality standards which are produced by appropriate processes.

Some embodiments of the present invention provide an injectable pharmaceutical formulation comprising carboplatin, or a pharmaceutically acceptable derivative thereof; and a pharmaceutically acceptable vehicle, wherein the formulation is filled with optimal fill volume in vials having specific packaging configurations. In some embodiments, the injectable formulations of the present invention reduce the wastage of carboplatin. In certain embodiments, the formulations are filled at optimal fill volumes in vials having specific packaging configurations to provide flexibility in dosing and to reduce the risk of contamination.

A further object of certain embodiments of the present invention is to provide an injectable pharmaceutical formulation comprising carboplatin, or a pharmaceutically acceptable derivative thereof; and a pharmaceutically acceptable vehicle, which remains physically and chemically stable when filled at an optimal fill volume in vials having specific packaging configurations and stored for an extended duration at room temperature. It is also an object some embodiments of the present invention to provide an injectable pharmaceutical formulation comprising carboplatin, or a pharmaceutically acceptable derivative thereof; and a pharmaceutically acceptable vehicle, filled at an optimal fill volume in vials having specific packaging configurations which remains free of microbial contamination without the use of a preservative.

Another object of certain embodiments of the present invention is to increase patient compliance by providing injectable pharmaceutical formulations comprising carboplatin, or a pharmaceutically acceptable derivative thereof; and a pharmaceutically acceptable vehicle; wherein the formulation is provided in a vial; and wherein the vial is filled to an optimal fill volume; and the vials have a specific packaging configuration. In some embodiments, the present invention enhances patient compliance and usability for healthcare practitioners at hospitals and clinics.

Yet another object of some embodiments of the present invention is to provide a process for preparing an injectable pharmaceutical formulation comprising carboplatin, or a pharmaceutically acceptable derivative thereof; and a pharmaceutically acceptable vehicle, wherein the injectable pharmaceutical formulation is filled in vials to an optimal fill volume; wherein the vials have a specific packaging configuration.

Further embodiments of the present invention provide methods of treating cancer in a patient in need thereof, comprising: providing an injectable formulation comprising carboplatin, or a pharmaceutically acceptable derivative thereof; and a pharmaceutically acceptable vehicle; wherein the formulation is filled at an optimal fill volume in vials having specific packaging configurations in an appropriate dose calculated on the basis of body surface area, glomerular filtration rate and target AUC so that wastage of the carboplatin is reduced; and patient and healthcare provider compliance is increased.

According to a further embodiments of the present invention, a stable pharmaceutical composition for injection is provided comprising: 10 mg/mL carboplatin, or a pharmaceutically acceptable derivative thereof; and a pharmaceutically acceptable vehicle having a pH in the range of 5 to 7; wherein the formulation is filled in vials (e.g., glass vials) at an optimal fill volume ranging from about 1 mL to about 75 mL; wherein the vials maintain a headspace in the range of about 20% to about 82%. In some embodiments, the packaging configuration is selected from, but not limited to, 20 mg/2 mL solution in vial of capacity 5 mL; 80 mg/8 mL solution in vial of capacity 10 mL; and 500 mg/50 mL solution in vial of capacity 50 mL. These exemplary packaging configurations of present invention minimize drug wastage, align with commonly prescribed dosages, reduce the need for multiple needle entries to lower contamination risks, enhance patient compliance and increase dosing flexibility.

Yet further embodiments of the present invention provide carboplatin formulations that are physically and chemically stable when filled in optimal fill volume in glass vials with specific packaging configurations and stored for extended periods of time at room temperature. In some embodiments, the formulations of present invention also remain substantially free, or free, of antimicrobial contamination without the use of a preservative, even in multi-dose vials; in particular, when the formulations are filled and supplied at an optimal fill volume in glass vials of specific configuration.

Other embodiments of the present invention provide processes for preparing the carboplatin formulations described herein involving the use of oxygen gas such that headspace is filled with oxygen gas and the dissolved oxygen content in the formulation is maintained at a certain level (e.g., not less than 28 PPM).

DETAILED DESCRIPTION

Carboplatin injection is widely used for treatment of cancer. The dose of carboplatin varies and depends on, for example, the body surface area (BSA), target AUC and glomerular filtration rate (GFR) of the patient. The packaging configurations of commercially available carboplatin formulations are not sufficient to cater to the variety of dosing requirements. Sometimes the dosing requirement is low, which leads to wastage of the formulation and sometimes the dosing requirement is high which requires the healthcare provider to administer the formulation from multiple vials which may present challenges in adherence to the prescribed treatment regimen. To arrive at a packaging configuration which solves both the problems of wastage and non-compliance, the present inventors, after extensive evaluation of various possible packaging configurations, identified optimal fill volumes, which are a component of the innovative packaging configurations of the present invention.

Injectable carboplatin formulations are aqueous formulations that may pose stability issues. To arrive at a storage stable aqueous solution of carboplatin that is free of instability problems (e.g., particulate matter after extended storage), the present inventors have also identified appropriate manufacturing processes to mitigate these issues.

As used herein, the term "Optimal Fill Volume (OFV)" refers to the amount of carboplatin formulation contained in each vial, carefully calibrated to deliver the desired therapeutic dose while maximizing usage and minimizing wastage. The selection of the optimal fill volume for each vial is crucial in reducing the need to discard excess medication and ensuring that each vial contains the right amount required for patient treatment. The present inventors conducted numerous experiments to determine the optimal fill volume for vials of different sizes. This was done by considering factors such as the nominal fill volumes, overflow volumes, in-process fill volume controls, and the gross content limits of the vials. The resulting headspace and required oxygen levels were also considered to maintain the stability of the formulation, while ensuring compliance with FDA requirements.

As used herein, the term "packaging configuration" refers to vials filled with the optimal fill volume (OFV) of the carboplatin formulations described herein. Each vial is designed to contain a specific fill volume that delivers the required therapeutic dose while minimizing wastage. The availability of multiple packaging configurations allows for precise dosing adjustments, ensuring efficient drug utilization and reducing the need for excess medication disposal.

As used herein, the term "capacity" in the context of vial capacity refers to the vendor nominal fill volume.

Embodiments of the present invention aim to minimize the wastage of carboplatin by filling the formulation at an optimal fill volume in specific vial configurations to better align with prescribed dosage requirements. The reduction of drug wastage is quantified using a Waste Reduction Efficiency Factor (WREF), which is defined as the percentage decrease in the volume of unused drug per dose when utilizing vial sizes according to certain embodiments of the present invention as compared to commercially available vial sizes.

In other words, WREF quantifies the improvement in drug utilization efficiency by comparing the percentage reduction in drug wastage between commercially available vials and the vials of the present invention. It is defined as the percentage decrease in wastage achieved by the optimized vials relative to the commercially available vials.

The WREF is calculated and expressed, according to the present invention, as per the following steps and formula:

$$WREF = Wc - Wp$$

where:
Wc=% drug wastage using commercially available vials
Wp=% drug wastage using the optimized vials of the present invention
WREF=Efficiency in waste reduction, expressed as a percentage Calculation of Wc and Wp:
Wc (Commercial Wastage %) is determined by calculating the excess drug remaining after administration when using currently available vial sizes, using the formula:

$$Wc = \frac{\left(\begin{array}{c}\text{Total drug available from '}n\text{' commercial vials} - \\ \text{Prescribed dose}\end{array}\right)}{\text{Prescribed dose}} \times 100$$

Wp (Optimized Wastage %) is determined similarly, but using the optimized vial sizes of the present invention:

$$Wp = \frac{\left(\begin{array}{c}\text{Total drug available from '}n\text{' vials of present invention} - \\ \text{Prescribed dose}\end{array}\right)}{\text{Prescribed dose}} \times 100$$

Some embodiments of the present invention demonstrate an improved efficiency in reducing drug wastage while maintaining accurate dosing and administration of drug.

As used herein, the term "head space percentage" or "head space %" refers to the percentage of void space in a vial calculated using the following formula:

$$\frac{\text{Vendor Overflow Volume} - \text{Target Fill Volume}}{\text{Vendor Overflow Volume}}$$

As used herein, the terms "infusing" and "purging" may be used interchangeably and refer to the process by which a gas (e.g., oxygen gas) is introduced into water for injection, compounding mass or solution in a closed system (e.g., a vial). For example, bubbling or otherwise passing the desired gas through a solution under atmospheric pressure to saturate the liquid and headspace with optimum quantities of the gas (e.g., oxygen).

The term "patient compliance", according to present invention, refers to the administration of a therapeutic dose of carboplatin using an optimal number of vials (n) containing the injectable carboplatin formulation to ease the method of administration for healthcare providers thereby increasing the patient and healthcare provider compliance at the time of administration leading to enhanced adherence to the prescribed treatment regimen. The fewer vials administered per day during the treatment cycle, the greater the patient compliance.

The term "accelerated storage condition" as used herein means subjecting the injectable formulations of present invention to 40° C./75% RH for up to 6 months. To perform the test, the injectable formulations are prepared, then filled in glass vials of specific sizes and kept in upright and inverted positions at 40° C./75% RH for between 1 month to 6 months. The upright and inverted vials are visually observed for any discoloration, precipitation or crystal formation. Presence of discoloration, precipitation or crystal formation is an indicator of instability. The injectable formulations that endure 40° C./75% RH for 6 months without any precipitation, and are supported by room temperature data, are found to be and therefore considered to be stable for 24 months when stored at room temperature.

The term "stable" as used herein means that the injectable formulations of the present invention are physically and chemically stable when stored for extended periods of time (e.g., at least 24 months). The physically stable formulation means that when the formulation of present invention comprising aqueous solution of carboplatin is filled in glass containers with optimal fill volume and is subjected to accelerated storage conditions, the aqueous solution shows no sign of precipitation or crystal formation or discoloration. Additionally, the formulation of present invention does not show any appearance of particulate matter when stored for extended periods of time (e.g., at least 24 months) and thus maintains physical stability.

The term 'chemically stable' as used herein means that the aqueous solution of carboplatin shows acceptable levels of known and unknown impurities during the shelf life of the product, particularly when stored at room temperature for at least 24 months. The terms "longer duration" or "extended duration" are used interchangeably and refer to a period of 24 months.

The term "room temperature" refers to 25° C.

According to certain embodiments, formulations of the present invention include the known impurity 1,1-cyclobutanedicarboxylic acid at not more than 1.0%, by weight of carboplatin and total degradation impurities at not more than 2.5%, by weight of carboplatin, when stored at room temperature for 24 months, optionally when protected from light.

In some embodiments, the formulations of present invention comprise carboplatin, or a pharmaceutically acceptable derivative thereof, in a concentration of from about 5 mg/mL to 15 mg/mL. In other embodiments, the concentration of carboplatin in the formulations of present invention is about 10 mg/mL.

In further embodiments, the formulations of present invention further comprise a pharmaceutically acceptable vehicle. In certain embodiments, the pharmaceutically acceptable vehicle comprises water for injection (WFI), which provides an inert, biocompatible medium ensuring solubility and stability of the carboplatin. WFI is a highly purified, sterile, and pyrogen-free water source, meeting stringent pharmacopeial standards such as USP and Ph. Eur. for pharmaceutical use.

While developing the injectable carboplatin formulations of the present invention, the inventors discovered that infusing oxygen into the formulation imparts greater stability. In come embodiments, the carboplatin composition was infused or purged with oxygen in order to achieve dissolved oxygen (DO) levels of at least 28 ppm, which resulted in improved chemical stability as compared to formulations infused or purged with nitrogen, which exhibited particulate matter formation during stability testing. In some embodiments, the present invention provides processes for preparing stable injectable formulations comprising carboplatin, or a pharmaceutically acceptable derivative thereof; and a pharmaceutically acceptable vehicle, comprising the steps of:

(i) providing water for injection at a temperature of about 20° C. to about 25° C.;
(ii) dissolving an effective amount of carboplatin in the water for injection;
(iii) making up the volume of solution to desired level;
(iv) purging the solution with oxygen gas to achieve a dissolved oxygen level of not less than 28 ppm
(v) buffering the solution to a pH of about 5 to about 7;
(vi) filtering the solution with a 0.22 µm filter;
(vii) filling the carboplatin solution in a glass vial;
(viii) stoppering the vial with a headspace oxygen flush; and
(ix) sealing the vial.

In some embodiments of the present invention, the process of preparing an injectable carboplatin formulation comprises a step wherein oxygen gas is purged continuously so that the level of dissolved oxygen is maintained in the solution at not less than 28 ppm and a final flushing of oxygen is done in the headspace.

In some embodiments, the pH of the carboplatin formulation is greater than 4, optionally from about 5 to about 7.

In certain embodiments, the formulations of the present invention comprising carboplatin, or a pharmaceutically acceptable derivative thereof, and WFI, are substantially free, or free, from preservatives. In these embodiments, despite the absence of preservatives, the formulations remain free of microbial contamination, even when a single vial is used for the administration of multiple doses to achieve the required therapeutic dose.

In other embodiments, the stable pharmaceutical formulations of the present invention, prepared using the oxygen purging processes described above, are filled to an optimal volume in Type I tubular amber glass vials. In further embodiments, the vials are available in different capacities (e.g., from 1 mL to 100 mL, 1 mL to 85 mL, or 1 mL to 55 mL), allowing for various optimal fill volumes of the carboplatin formulation. In some embodiments, vials used in accordance with the present invention are sealed with sterilized twenty (20) mm stoppers.

In some embodiments, the process of preparing the carboplatin formulations of the present invention and their filling in suitable vials is carried out under aseptic sterilization processes, ensuring the sterility of the formulations and preventing contamination.

In other embodiments, the carboplatin formulations of the present invention, when stored at room temperature for two years and protected from light, remain stable such that the content of the known impurity 1,1-cyclobutanedicarboxylic acid does not exceed 1.0%, by weight of carboplatin, and the total degradation impurities do not exceed 2.5%, by weight of carboplatin.

According to some embodiments, a packaging configuration according to the present invention comprises a 20 mg/2 mL of an injectable carboplatin formulation. In some embodiments, the formulation is designed with a gross content limit of approximately 2.15 mL to 2.35 mL with a target fill volume of 2.218 mL representing the optimal fill volume, wherein 20 mg of carboplatin is dissolved in a sufficient amount of WFI. In some embodiments, the solution is filled into Type I tubular amber glass vials with a 5 mL capacity, with the headspace in the range of about 77% to about 82% and dissolved oxygen content of not less than 28 ppm to maintain formulation stability.

In further embodiments of the present invention, an injectable carboplatin formulation (10 mg/mL strength) is filled at an optimal volume of 2.2 mL, maintaining a strength of 20 mg/2 mL. In certain embodiments, the headspace can be as high as 81.5%, and the formulation is packaged in 5 mL capacity vials, providing a new configuration suitable for precise low-dose administration to patients in need.

Currently, the lowest commercially available strength is 50 mg/5 mL. Therefore, to address the needs of patients requiring doses lower than 50 mg and to minimize the challenges in combining low strength and high strength vials to achieve the therapeutic dose, embodiments of the present invention introduce a new packaging configuration with a strength of 20 mg/2 mL of carboplatin, offering improved dosing flexibility and reduced drug wastage.

According to other embodiments, a packaging configuration of the present invention comprises 80 mg/8 mL of injectable carboplatin formulation. In some embodiments, the injectable carboplatin formulation is designed with a gross content limit of approximately 8.2 mL to 8.8 mL with a target fill volume of 8.55 ml representing the optimal fill volume, where 80 mg of carboplatin is dissolved in a sufficient amount of WFI. In certain embodiments, the solution is filled into Type I tubular amber glass vials with a 10 mL capacity, with the headspace in the range of from about 47% to 57% and dissolved oxygen content of no less than 28 PPM to maintain formulation stability.

In some embodiments, the injectable carboplatin formulation (10 mg/mL strength) is filled at an optimal fill volume of 8.55 mL, maintaining a strength of 80 mg/8 mL. The headspace can be as high as 57%, and the formulation can be packaged in 10 mL capacity vials, providing a new configuration suitable for precise low-dose administration to patients in need.

According to other embodiments, the present invention provides packaging configurations comprising a 500 mg/50 mL of injectable carboplatin formulation. In some embodiments, the formulation is designed with a gross content limit of approximately 50.30 mL to 55.30 mL with a target fill volume of about 51.508 mL representing the optimal fill volume, where 500 mg of carboplatin is dissolved in a sufficient amount of WFI. In certain embodiments, the solution is filled into Type I tubular amber glass vials with a 50 mL capacity, with the headspace in the range of about 20% to 30% and dissolved oxygen content of no less than 28 PPM to maintain formulation stability.

In some embodiments, the injectable carboplatin formulation (10 mg/mL strength) is filled at an optimal volume of 51.5 mL, maintaining a strength of 500 mg/50 mL. In some embodiments, the headspace can be as high as 29.2%, and the formulation is packaged in 50 mL capacity vials, providing a new configuration suitable for precise low-dose administration to patients in need.

According to further embodiments, the vials implementing the new packaging configuration of the present invention are presented as individual packs reducing the wastage of drug such that WREF is maximized, and patient compliance is improved. In some embodiments, the new packaging configurations ensure that a minimum number of vials are administered to the patient per day during the treatment cycle while still achieving the therapeutic dose required by the patient.

In other embodiments, the vials implementing the new packaging configuration of the present invention are presented as multipacks, where multiple vials of the same or different configurations are packaged together in a single pack providing dosing flexibility; enhanced patient compliance; and reduced wastage of drug, such that WREF is maximized.

Some embodiments of the present invention provide stable pharmaceutical formulations comprising carboplatin, or a pharmaceutically acceptable derivative thereof, and a pharmaceutically acceptable vehicle, wherein the formulations are provided in new packaging configurations of vials containing optimized fill volumes. In some embodiments, the vials of present invention significantly reduce drug wastage, which is measured, as per the present invention, in terms of Waste Reduction Efficiency Factor (WREF). The WREF according to certain embodiments of the present invention may be up to 500%, or range from about 0% to about 500%, optionally from about 0.1% to about 500%, about 1% to about 450%, about 5% to about 400%, about 10% to about 350%, about 25% to about 300%, about 50% to about 250%, or greater than about 1%, 5%, 10%, 20%, 25%, 50%, 75%, 100%, 150%, 200% or 250%.

In further embodiments, the stable pharmaceutical formulations of the present invention comprise carboplatin, or a pharmaceutically acceptable derivative thereof; and a pharmaceutically acceptable vehicle, with new packing configurations of vials each containing an optimum fill volume, which improves patient compliance as measured in terms of the number of vials used to deliver the required therapeutic dose to the patient, during the treatment cycle. The fewer the number of vials, the greater the likelihood of patient and healthcare provider compliance. In some embodiments, the number of vials administered to the patient per day during the treatment cycle is from about 1 to about 15 vials, optionally from about 1 to about 14 vials, about 1 to about 13 vials, about 1 to about 12 vials, about 1 to about 11 vials, about 1 to about 10 vials, about 1 to about 9 vials, about 1 to about 8 vials, about 1 to about 7 vials, about 1 to about 6 vials, about 1 to about 5 vials; or about 1 vial, about 2 vials, about 3 vials, about 4 vials, about 5 vials, about 6 vials, about 7 vials, about 8 vials, about 9 vials, about 10 vials, about 11 vials, about 12 vials, about 13 vials, about 14 vials, or about 15 vials.

In some embodiments, if the WREF is below 0%, the number of vials of the present invention required to achieve a therapeutic dose are less than the number of commercially available vials required to achieve a therapeutic dose and in some cases it fulfils the need of providing the required dosage where there is lack of availability of necessary commercial pack sizes needed to fulfil the dosage requirements of an individual patient.

In some embodiments, the present invention provides a stable injectable carboplatin formulation comprising: (i) 10 mg/mL of carboplatin, or a pharmaceutically acceptable derivative thereof, and (ii) a pharmaceutically acceptable vehicle having a pH of from about 5 to about 7. In some embodiments, the injectable carboplatin formulations of the present invention are prepared using an oxygen purging process such that the formulations contain a dissolved oxygen content of not less than about 28 PPM; wherein the formulations are filled at an optimal fill volume of from about 2.15 mL to about 55.30 mL in vials having a capacity of from about 5 mL to about 50 mL; wherein the formulations maintain stability in the vials such that 1,1-cyclobutanedicarboxylic acid is present at not more than 1.0% by weight of carboplatin and total degradation impurities are not more than 2.5% by weight of carboplatin when stored at room temperature for 24 months; optionally wherein the WREF is up to about 500%; further optionally wherein the number of vials administered to a patient per day during the treatment cycle is from about 1 to about 15. In some embodiments, the present invention provides packaging configurations that enable methods that use fewer vials per day during a treatment cycle than currently available packaging configurations and/or vials.

In certain embodiments, the present invention provides stable pharmaceutical formulations for injection comprising: carboplatin, or a pharmaceutically acceptable derivative thereof; and a pharmaceutically acceptable vehicle; wherein the formulations can be diluted to concentrations as low as 0.5 mg/mL with 5% D5W or 0.9% Sodium Chloride Injection, USP. In other embodiments, the formulations of the present invention maintain stability after dilution with 5% D5W or 0.9% Sodium Chloride Injection, USP for at least 8 hours after dilution.

In some embodiments, the present invention provides a parenteral product comprising: a vial having capacity to hold from about 1 mL to about 100 mL; and a composition comprising: about 10 mg/mL of carboplatin, or a pharmaceutically acceptable derivative thereof, and a pharmaceutically acceptable vehicle; wherein the composition has a pH of from about 5 to about 7 and contains dissolved oxygen levels of not less than 28 PPM; wherein the vial contains from about 1 mL to about 70 mL of said composition and has a head space ranging from 20%-82% of the vial capacity; wherein the head space comprises oxygen; wherein the composition comprises less than about 1.0% wt. % of 1,1-cyclobutanedicarboxylic acid; and wherein the composition comprises not more than 2.5 wt. % of total degradation impurities after twenty-four months at room temperature.

In further embodiments, the present invention provides methods for treating patients suffering from cancer comprising: administering a formulation as described herein, comprising carboplatin. In some embodiments, the carboplatin is administered as a single agent at a therapeutic dose calculated based on body surface area, target AUC and glomerular filtration rate. In other embodiments, the injectable carboplatin formulation is administered to a patient suffering from recurrent ovarian carcinoma, as a single agent using vials having new packaging configurations, at a dosage of 360 mg/m$^2$ IV on day 1 every 4 weeks; wherein the therapeutic does is achieved by using an optimal number of vials having different configurations to enhance patient compliance.

In some embodiments, the present invention provides a method for treating advanced ovarian cancer comprising: administering an injectable carboplatin formulation to a patient in need thereof, using vials having new packaging configurations as described herein, at a dosage of 300 mg/m² IV on day 1 every 4 weeks for 6 cycles, as combination therapy with cyclophosphamide; wherein the therapeutic dose is achieved by using an optimal number of vials having different configurations to enhance patient compliance.

The invention will now be further described by the following examples, which are illustrative rather than limiting.

EXAMPLES

Example 1: Composition of Exemplary Formulation of Present Invention

TABLE 1

| S. No. | Ingredient | Quantity (mg) | | |
|---|---|---|---|---|
| 1 | Carboplatin | 20.00 | 80.00 | 500.00 |
| 2 | Water for injection | q.s to 2 mL | q.s to 8 mL | q.s to 50 mL |

Process of preparation: The product manufacturing process begins with dispensing of water for injection into the vessel, then bubbling of filtered oxygen into the solution to reach dissolved oxygen content greater than 28 parts per million (PPM). The dispensed API was transferred to water of above step. Under continuous oxygen blanketing, mix the solution for 30 minutes or until a clear solution is obtained. Volume of solution made to 100% of batch size by using oxygen purged water. Filter the bulk solution through a 0.22 micron sterile filter. About 2 mL of the prepared solution is filled in vials of 5 mL capacity; about 8 mL of the prepared solution is filled in vials made of amber tubular Type-1 glass of 10 mL capacity; and 50 mL of prepared solution was filled in vials of amber tubular Type-1 glass of 50 mL capacity, followed by overlaying oxygen gas in the headspace of glass vials and stoppered with sterilized 20 mm stoppers. The step is followed by visual inspection, labelling, and packing. The entire manufacturing is carried out under subdued or sodium vapor lamp.

Example 2: Effect of Oxygen Purging on Stability

Example 2.1: Stability Data of Formulation Prepared by Oxygen Purging

An exemplary formulation of the present invention (see, e.g., Example 1) was subjected to stability studies to evaluate the effect of oxygen purging. The results are described in Table 2 (below):

TABLE 2

| | | | | 40° C./75% RH | |
|---|---|---|---|---|---|
| S. No. | Tests | Specification | Initial | 60° C./7 days | 2 M | 3 M |
| 1 | Description | A clear colorless to pale yellow solution | Clear colorless solution free of visible particles | Clear colorless solution free of visible particles | Clear colorless solution free of visible particles | Clear colorless solution free of visible particles |
| 2 | pH | 5.0 to 7.0 | 5.61 | 5.53 | 5.67 | 5.59 |
| 3 | Assay, % | 90-110 | 102.3 | 98.58 | 100.36 | 99.7 |
| 4 | Impurities | | | | | |
| | 1,1-cyclobutanedicarboxylic acid (CBDCA), % | NMT 1.0% | 0.115 | 0.395 | 0.293 | 0.314 |
| | Cyclobutanemonocarboxylic acid | NMT 0.2% | ND | ND | ND | ND |
| | Organic Impurities | NMT 0.2% | ND | ND | ND | ND |
| | Total degradation products | NMT 2.5% | ND | ND | ND | ND |
| 5 | Particulate matter | | | | | |
| | Sub visible particles | 10 um ≤ 6000 | 580 | 1224 | 1322 | 621 |
| | | 25 um ≤ 600 | 40 | 80 | 169 | 47 |
| | Color Absorbance at 440 nm | NMT 0.200 | 0.002 | 0.024 | 0.005 | 0.009 |

As confirmed by the data described in Table 2 (above), there is no change observed in the color of the solution, and the solution is also free from visible fibres and particles with impurities well within specified limits. Accordingly, the exemplary carboplatin injection of the present invention is both physically and chemically stable.

Example 2.2. Stability Data of Formulation Prepared by Nitrogen Purging

TABLE 3

| S. No. | Tests | Specification | Initial | 60° C./7 days | 40° C./75% RH | |
|---|---|---|---|---|---|---|
| | | | | | 2 M | 3 M |
| 1 | Description | A clear colorless to pale yellow solution | A clear, colorless solution, free from visible particles | A pale yellow color solution with suspended black particles | A yellowish color solution with suspended fibers | A yellowish color solution with black particles |
| 2 | pH | 5.0 to 7.0 | 5.58 | 5.65 | 5.83 | 5.84 |
| 3 | Assay, % | 90-110 | 101.97 | 98.00 | 100.4 | 99.12 |
| 4 | Impurities | | | | | |
| | 1,1-cyclobutanedicarboxylic acid (CBDCA) | NMT 1.0% | 0.120 | 0.529 | 0.315 | 0.305 |
| | Cyclobutanemonocarboxylic acid | NMT 0.2% | ND | ND | ND | ND |
| | Organic Impurities | NMT 0.2% | ND | ND | ND | ND |
| | Total degradation products | NMT 2.5% | ND | ND | ND | ND |
| 5 | Particulate matter | | | | | |
| | Sub visible particles | 10 um ≤ 6000 | 2572 | 17313 | 951 | NA |
| | | 25 um ≤ 600 | 204 | 254 | 218 | |
| | Color Absorbance at 440 nm | NMT 0.200 | 0.149 | 0.149 | 0.061 | 0.1 |

As shown from the data described in Table 3 (above), there is significant change in the color of the solution with black particles observed when oxygen is replaced with nitrogen. As such, carboplatin injection is not compatible with nitrogen gas.

Example 2.3. Stability Data of Formulation without Nitrogen or Oxygen Purging

TABLE 4

| S. No. | Tests | Specification | Initial | 60° C./7 days | 40° C./75% RH | |
|---|---|---|---|---|---|---|
| | | | | | 2 M | 3 M |
| 1 | Description | A clear colorless to pale yellow solution | A clear, colorless solution, free from visible particles | A pale yellow color solution with suspended fibers | A pale yellow color solution with suspended fibers | A pale yellow color solution with suspended fibers |
| 2 | pH | 5.0 to 7.0 | 5.67 | 5.75 | 5.73 | 5.77 |
| 3 | Assay % | 90-110 | 101.7 | 97.21 | 99.78 | 98.17 |
| 4 | Impurities | | | | | |
| | 1,1-cyclobutanedicarboxylic acid (CBDCA) | NMT 1.0% | 0.112 | 0.380 | 0.296 | 0.278 |
| | Cyclobutanemonocarboxylic acid | NMT 0.2% | ND | ND | ND | ND |
| | Organic Impurities | NMT 0.2% | ND | ND | ND | ND |
| | Total degradation products | NMT 2.5% | ND | ND | ND | ND |

TABLE 4-continued

|  |  |  |  |  | 40° C./75% RH | |
|---|---|---|---|---|---|---|
| S. No. | Tests | Specification | Initial | 60° C./7 days | 2 M | 3 M |
| 5 | Particulate matter | | | | | |
|  | Sub visible particles | 10 um ≤ 6000 | 3752 | 1047 | 288 | 212 |
|  |  | 25 um ≤ 600 | 56 | 11 | 63 | 11 |
|  | Color Absorbance at 440 nm | NMT 0.200 | 0.002 | NA | 0.022 | 0.039 |

There are no significant changes observed in accelerated condition (40° C./75% RH) up to 3 months without replacing of oxygen except description test where suspended fibers are observed. Thus, carboplatin injection does not appear to be physically stable without purging with gas. Further, the observations described in Table 4 (above) demonstrate that certain levels of oxygen prevent the formation of fibres and particles during accelerated aging (40° C./75% RH), which confirms its role in stabilizing carboplatin solutions.

Example 3: Selection of Optimal Fill Volume and Determination of Headspace

The selection of optimal fill volume of 10 mg/mL carboplatin solution to be filled in the vials of different capacities is based on the actual vial capacity, the finished product gross content limits and in-process fill volume controls in consideration of USFDA acceptance criteria.

The optimum fill volumes for the packaging configurations of present invention are based on the extractable volume study performed at the finished product manufacturing site. Fill volume determination studies are performed for carboplatin injection (10 mg/mL) prepared according to Example 1, for different fill volumes. The procedure further includes the following:
  i. 3 vials of each fill volume are prepared.
  ii. Transferred the exact quantity of water into each vial following the instructions and being compliant with the acceptance criteria
  iii. Verification of the extractable volume of all the prepared vials is done.

The extractable volume has been measured for all fill volumes and average results are given below in Table 5, for all the packaging configurations of 20 mg/2 mL, 80 mg/8 mL and 500 mg/50 mL:

TABLE 5

| | Packaging | | Process Fill Volume Controls per Vial | | | FP Gross | |
|---|---|---|---|---|---|---|---|
| S. No. | Configuration of Present Invention | Vial Capacity (mL) | Optimized Fill Volume (mL) | Control Limits (mL) | Action Limits (mL) | Content Limits (mL) | Headspace % |
| 1 | 20 mg/2 mL | 5 | 2.218 | 2.184-2.250 | 2.150-2.283 | 2.150-2.350 | 81.50% |
| 2 | 80 mg/8 mL | 10 | 8.55 | 8.422-8.678 | 8.234-8.808 | 8.200-8.800 | 56.80% |
| 3 | 500 mg/50 mL | 50 | 51.508 | 50.736-52.281 | 50.478-52.538 | 50.300-55.300 | 29.20% |

The percentage (%) headspace is calculated using a formula as described hereinabove. It depends on the target/optimized fill volume and the overflow volume of each vial capacity. For a 5 mL capacity vial, overflow volume may be 10 to 12 mL, whereas it may be 16.2 mL to 19.8 mL for a 10 mL vial and 64.8 ml to 72.8 mL for a 50 mL vial. The % head space in the above table is based on highest overflow volume of each vial capacity in conjunction with target or optimized fill volume. It is not directly the same as vial capacity and so it is to be arrived at based on the experimental data for various packaging configurations.

Example 4: Stability of Vials of New Configurations with New Strengths

Vials having the new packaging configuration according to certain embodiments of the present invention (20 mg/2 mL, 80 mg/8 mL and 500 mg/ea mL) are kept inverted under accelerated aging conditions to evaluate stability. The results of the studies are depicted below in Tables 6 to 8 (below):

Example 4.1: Stability of Vials Containing Formulation of Strength 20 mg/2 mL

TABLE 6

| S. No. | Tests | Specification | Initial | 40° C./75% RH (Inverted) 1 M | 3 M | 6 M |
|---|---|---|---|---|---|---|
| 1 | Description | A clear colorless to pale yellow solution | A Clear, Colorless Solution | A Clear, Colorless Solution | A Clear, Colorless Solution | A Clear, Colorless Solution |
| 2 | pH | 5.0 to 7.0 | 6.9 | 6.0 | 6.4 | 6.1 |
| 3 | Assay, % | 90-110 | 99.5 | 98.4 | 97.3 | 97.8 |
| 4 | Impurities | | | | | |
| | Limit of 1,1- cyclobutanedicarboxylic acid | | | | | |
| | Content of 1,1-cyclobutane dicarboxylic acid (CBDCA) | NMT 1.0% | 0.2 | 0.2 | 0.3 | 0.5 |
| | Cyclobutane monocarboxylic acid | NMT 0.2% | ND | ND | ND | ND |
| | Organic Impurities | | | | | |
| | Cisplatin | NMT 0.2% | ND | ND | ND | ND |
| | Any unspecified degradation product | NMT 0.2% | ND | ND | ND | ND |
| | Total degradation products (Include the amount of 1,1 Cyclobutane dicarboxylic acid and Cyclobutane monocarboxylic acid) | NMT 2.5% | 0.2 | 0.2 | 0.3 | 0.6 |
| 5 | Particulate Matter | | | | | |
| | Sub visible particles | 10 um ≤ 6000 | 3 | 2 | 5 | 4 |
| | | 25 um ≤ 600 | 0 | 0 | 0 | 0 |
| 6 | Color Absorbance at 440 nm | NMT 0.200 | 0.003 | 0.002 | 0.012 | 0.026 |

Example 4.2: Stability of Vials Containing Formulation of Strength 80 mg/8 mL

TABLE 7

| S. No. | Tests | Specification | Initial | 40° C./75% RH (Inverted) 1 M | 3 M | 6 M |
|---|---|---|---|---|---|---|
| 1 | Description | A clear colorless to pale yellow solution | A Clear, Colorless Solution | A Clear, Colorless Solution | A Clear, Colorless Solution | A clear pale yellow solution |
| 2 | pH | 5.0 to 7.0 | 6.7 | 6.2 | 6.1 | 6.3 |
| 3 | Assay, % | 90-110 | 100.6 | 98.8 | 97.4 | 97.6 |
| 4 | Impurities | | | | | |
| | Limit of 1,1- cyclobutanedicarboxylic acid | | | | | |
| | Content of 1,1-cyclobutanedicarboxylic acid (CBDCA), % | NMT 1.0% | 0.1 | 0.2 | 0.3 | 0.4 |
| | Cyclobutanemonocarboxylic acid | NMT 0.2% | ND | ND | ND | 0.1 |

TABLE 7-continued

|  |  |  |  | 40° C./75% RH (Inverted) | | |
|---|---|---|---|---|---|---|
| S. No. | Tests | Specification | Initial | 1 M | 3 M | 6 M |
| | Organic Impurities | | | | | |
| | Cisplatin | NMT 0.2% | ND | ND | ND | ND |
| | Any unspecified degradation product | NMT 0.2% | ND | ND | ND | ND |
| | Total degradation product (Include the amount of 1,1 Cyclobutane dicarboxylic acid and Cyclobutane mono carboxylic acid) | NMT 2.5% | 0.1 | 0.2 | 0.3 | 0.5 |
| 5 | Particulate Matter | | | | | |
| | Sub visible particles | 10 um ≤ 6000 | 12 | 13 | 21 | 27 |
| | | 25 um ≤ 600 | 0 | 0 | 0 | 0 |
| 6 | Color Absorbance at 440nm | NMT 0.200 | 0.003 | 0.004 | 0.009 | 0.024 |

Example 4.3: Stability of Vials Containing Formulation of Strength 500 mg/50 mL

TABLE 8

|  |  |  |  | 40° C./75% RH (Inverted) | | |
|---|---|---|---|---|---|---|
| S. No. | Tests | Specification | Initial | 1 M | 3 M | 6 M |
| 1 | Description | A clear colorless to pale yellow solution | A Clear, Colorless Solution | A Clear, Colorless Solution | A Clear, Colorless Solution | A Clear pale yellow solution |
| 2 | pH | 5.0 to 7.0 | 6.8 | 6.2 | 6.0 | 6.4 |
| 3 | Assay, % | 90-110 | 101.1 | 98.9 | 97.6 | 97.9 |
| 4 | Impurities | | | | | |
| | Limit of 1,1- cyclobutanedicarboxylic acid | | | | | |
| | Content of 1,1-cyclobutanedicarboxylic acid (CBDCA), % | NMT 1.0% | 0.1 | 0.2 | 0.3 | 0.3 |
| | Cyclobutanemonocarboxylic acid | NMT 0.2% | ND | ND | ND | 0.1 |
| | Organic Impurities | | | | | |
| | Cisplatin | NMT 0.2% | ND | ND | ND | ND |
| | Any unspecified degradation product | NMT 0.2% | ND | ND | ND | ND |
| | Total degradation product (Include the amount of 1,1 Cyclobutane dicarboxylic acid and Cyclobutane mono carboxylic acid) | NMT 2.5% | 0.1 | 0.2 | 0.3 | 0.4 |
| 5 | Particulate Matter | | | | | |
| | Sub visible particles | 10 um ≤ 6000 | 23 | 77 | 163 | 33 |
| | | 25 um ≤ 600 | 0 | 0 | 0 | 0 |
| 6 | Color Absorbance at 440 nm | NMT 0.200 | 0.003 | 0.003 | 0.011 | 0.028 |

As illustrated by the data described in Tables 6 to 8 (above), vials having the packaging configuration in accordance with embodiments of the present invention comprising an injectable carboplatin formulation prepared using an oxygen purging process are stable under accelerated aging conditions. These results confirm that exemplary injectable carboplatin formulations of the present invention are stable at room temperature for 24 months protected from light.

Example 5: Evaluations of Drug Wastage

The therapeutic dose of patient for carboplatin is determined by, for example, body surface area, glomerular filtration rate and target AUC. It is calculated using Calvert formula.

Based on a multifactored evaluation, the dosages evaluated in the examples below are 115 mg, 125 mg, 150 mg, 230 mg, 250 mg, 300 mg, 345 mg, 375 mg, 450 mg, 460 mg, 500 mg, 575 mg, 600 mg, 625 mg, 690 mg, 750 mg and 900 mg.

The examples below describe the results of comparative evaluations in reduction of wastage between commercially available vials and vials having an exemplary configuration according to certain embodiments of the present invention at variable doses which are calculated based on the above criteria and Calvert formula. Wastage is measured in terms of the Wastage Reduction Efficiency Factor (WREF). The data takes into account the optimum number of vials required based on the formulation strengths used to deliver the therapeutic dose while ensuring both patient and healthcare provider compliance.

Example 5.1: Dose=115 mg; GFR=90 mL/min; Target AUC=1 mg/mL·min

TABLE 9

| Number × Strength of Commercial Vials (mg/mL) | Total Drug (mg) | Drug Waste or Carryover (mg) | % Wastage (Wc) | Number × Strength of Exemplary Vials* (mg/mL) | Total Drug (mg) | Drug Waste or Carryover (mg) | % Wastage (Wp) | WREF (%) = Wc − Wp |
|---|---|---|---|---|---|---|---|---|
| 3 × (50 mg/5 mL) OR 1 × (150 mg/15 mL) | 150 | 35 | 30.4 | 2 × (20 mg/2 mL) + 1 × (80 mg/8 mL) OR | 120 | 5 | 4.35 | 26.04 |
| 1 × (450 mg/45 mL) | 450 | 335 | 291.3 | 6 × (20 mg/2 mL) | | | 4.35 | 286.95 |
| 1 × (600 mg/60 mL) | 600 | 485 | 421.7 | | | | 4.35 | 417.35 |

*Exemplary Vials = exemplary vials of the present invention

As illustrated by the data described in Table 9 (above), exemplary vial configurations in accordance with embodiments of the present invention significantly reduce drug wastage compared to commercially available vials. The reduction in wastage ranges from 26.04 to 417.3500, depending on the vial combination used to achieve the target therapeutic dose of 115 mg.

Example 5.2: Dose=125 mg; GFR=100 mL/min; Target AUC=1 mg/mL·min

TABLE 10

| Number × Strength of Commercial Vials (mg/mL) | Total Drug (mg) | Drug Waste or Carryover (mg) | % Wastage (Wc) | Number × Strength of Exemplary Vials* (mg/mL) | Total Drug (mg) | Drug Waste or Carryover (mg) | % Wastage (Wp) | WREF (%) = Wc − Wp |
|---|---|---|---|---|---|---|---|---|
| 3 × (50 mg/5 mL) OR | 150 | 25 | 20 | 2 × (20 mg/2 mL) + 1 × | 120 | 5 | 4 | 16 |
| 1 × (150 mg/15 mL) | | | | (80 mg/8 mL) OR | | | 4 | 16 |
| 1 × (450 mg/45 mL) | 450 | 325 | 260 | 6 × (20 mg/2 mL) | | | 4 | 256 |
| 1 × (600 mg/60 mL) | 600 | 475 | 380 | | | | 4 | 376 |

*Exemplary Vials = exemplary vials of the present invention

Based on the possible vial combinations, it can be inferred that the use of vials of the present invention significantly reduces drug wastage compared to commercially available vials. The reduction in wastage ranges from 16% to 376%, depending on the vial combination used to achieve the target therapeutic dose of 125 mg.

Example 5.3: Dose=150 mg; GFR=125 mL/min; Target AUC=1 mg/mL·min

TABLE 11

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 3 x (50 mg/5 mL) OR 1 x (150 mg/15 mL) | 150 | 0 | 0 | 4 x (20 mg/2 mL) + 1 x (80 mg/8 mL) OR 2 x (80 mg/2 mL) | 160 | 10 | 6.66 | −6.66 |
|  |  |  |  |  |  |  | 6.66 | −6.66 |
| 1 x (450 mg/45 mL) | 450 | 300 | 200 |  |  |  | 6.66 | 193.3 |
| 1 x (600 mg/60 mL) | 600 | 450 | 300 |  |  |  | 6.66 | 293.3 |

*Exemplary Vials = exemplary vials of the present invention

Based on the possible vial combinations, it can be inferred that the use of vials of the present invention generally reduces drug wastage compared to commercially available vials. The reduction in wastage ranges from (−) 6.66% to 293.3%, depending on the vial combination used to achieve the target therapeutic dose. For higher-volume vials, the present invention significantly reduces wastage, particularly in cases where large commercial vials (e.g., 450 mg or 600 mg) would otherwise lead to substantial drug loss.

Example 5.4: Dose=230 mg; GFR=90 mL/min; Target AUC=2 mg/mL·min

TABLE 12

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 5 x (50 mg/5 mL) OR 2 x (50 mg/5 mL) + 1 x (150 mg/15 mL) | 250 | 20 | 8.69 | 4 x (20 mg/2 mL) + 2 x (80 mg/8 mL) OR 3 x (80 mg/8 mL) | 240 | 10 | 4.3 | 4.39 |
| 2 x (150 mg/15 mL) | 300 | 70 | 30.4 |  |  |  |  | 26.1 |
| 1 x (450 mg/45 mL) | 450 | 220 | 95.6 |  |  |  |  | 91.3 |
| 1 x (600 mg/60 mL) | 600 | 370 | 160.8 |  |  |  |  | 156.5 |

*Exemplary Vials = exemplary vials of the present invention

Based on the possible vial combinations, it can be inferred that the use of vials from the present invention reduces drug wastage compared to commercially available vials. The reduction in wastage (WREF) ranges from 4.39% to 156.5%, depending on the vial combination used to achieve the target therapeutic dose. The most significant reduction is observed when replacing larger commercial vials (e.g., 450 mg or 600 mg), which otherwise result in substantial drug loss.

Example 5.5: Dose=250 mg; GFR=100 mL/min; Target AUC=2 mg/mL·min

TABLE 13

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 5 x (50 mg/5 mL) OR 2 x (50 mg/5 mL) + 1 x (150 mg/15 mL) | 250 | 0 | 0 | 1 x (20 mg/2 mL) + 3 x (80 mg/8 mL) | 260 | 10 | 4.3 | -10 |
| 2 x (150 mg/15 mL) | 300 | 50 | 20 | | | | | 10 |
| 1 x (450 mg/45 mL) | 450 | 200 | 80 | | | | | 70 |
| 1 x (600 mg/60 mL) | 600 | 350 | 140 | | | | | 130 |

*Exemplary Vials = exemplary vials of the present invention

Based on the possible vial combinations, it can be inferred that the use of vials from the present invention generally reduces drug wastage compared to commercially available vials, with WREF values ranging from −10% to 130%. For larger vial sizes (e.g., 450 mg and 600 mg), the present invention significantly reduces wastage, with a maximum reduction of 130%, demonstrating its advantage in minimizing excess drug loss.

Example 5.6: Dose=300 mg; GFR=90 mL/min; Target AUC=1 mg/mL·min

TABLE 14

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 6 x (50 mg/5 mL) OR 2 x (150 mg/15 mL) OR 3 x (50 mg/5 mL) + 1 x (150 mg/15 mL) | 300 | 0 | 0 | 4 x (80 mg/8 mL) | 320 | 20 | 6.66 | -6.66 |
| 1 x (450 mg/45 mL) | 450 | 150 | 50 | | | | | 43.34 |
| 1 x (600 mg/60 mL) | 600 | 300 | 100 | | | | | 93.34 |

*Exemplary Vials = exemplary vials of the present invention

Based on the possible vial combinations, it can be inferred that the use of vials from the present invention generally reduces drug wastage compared to commercially available vials, with WREF values ranging from (−)6.66% to 93.34%. For larger vial sizes (e.g., 450 mg and 600 mg), the present invention significantly reduces wastage, with a maximum reduction of 93.34%, highlighting its efficiency in minimizing drug loss.

Example 5.7: Dose=345 mg; GFR=90 mL/min;
Target AUC=1 mg/mL·min

TABLE 15

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 2 x (150 mg/15 mL) + 1 x (50 mg/5 mL) OR 7 x (50 mg/5 ml) | 350 | 5 | 1.44 | 4 x (80 mg/8 mL) + 2 x (20 mg/2 mL) | 360 | 15 | 4.34 | −2.9 |
| 1 x (600 mg/60 mL) | 600 | 255 | 73.9 | | | | | 73.9 |
| 1 x (450 mg/45 mL) OR 3 x (150 mg/15 mL) | 450 | 105 | 30.4 | | | | | 30.4 |

*Exemplary Vials = exemplary vials of the present invention

Based on the possible vial combinations, it can be inferred that the use of vials from the present invention effectively reduces drug wastage compared to commercially available vials, with WREF values ranging from (−29 to 73.9%. The highest reduction is observed when replacing large commercial vials (e.g., 600 mg), leading to a 73.90% decrease in wastage.

Example 5.8: Dose=375 mg; GFR=100 mL/min;
Target AUC=3 mg/mL·min

TABLE 16

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 2 x (150 mg/15 mL) + 2 x (50 mg/5 mL) OR 8 x (50 mg/5 mL) | 400 | 25 | 6.66 | 5 x (80 mg/8 mL) | 400 | 25 | 6.66 | 0 |
| 1 x (600 mg/60 mL) | 600 | 225 | 60 | | | | | 53.34 |
| 1 x (450 mg/45 mL) OR 3 x (150 mg/15 mL) | 450 | 75 | 20 | | | | | 13.34 |

*Exemplary Vials = exemplary vials of the present invention

Based on the possible vial combinations, it can be inferred that the use of vials from the present invention generally reduces drug wastage compared to commercially available vials, with WREF values ranging from 0% to 53.34%. Significant reductions in wastage are observed when replacing larger commercial vials (e.g., 600 mg), with a maximum decrease of 53.34. This highlights the efficiency of the present invention vials in minimizing unnecessary drug loss while maintaining dosing accuracy.

Example 5.9: Dose=450 mg; GFR=125 mL/min; Target AUC=3 mg/mL·min

TABLE 17

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 2 x (150 mg/15 mL) + 3 x (50 mg/5 mL) OR 1 x (450 mg/45 mL) OR 3 x (150 mg/15 mL) OR 9 x (50 mg/5 ml) | 450 | 0 | 0 | 1 x (500 mg/50 mL) | 500 | 50 | 11.11 | −11.11 |
| 1 x (600 mg/60 mL) | 600 | 150 | 33.33 | | | | | 22.22 |

*Exemplary Vials = exemplary vials of the present invention

Based on the possible vial combinations, it can be inferred that the use of vials from the present invention provides flexibility in drug administration while ensuring efficient utilization. The WREF values range from −11.11% to 22.22%, indicating that the present invention vials significantly reduce wastage, particularly in cases where larger commercial vials, such as the 600 mg option, are replaced, leading to a 22.22% reduction in wastage. In cases where WREF is −11.11%, the difference is marginal and compensated by the optimized vial strengths of the present invention, which can improve dosing accuracy and streamline inventory management.

Example 5.10: Dose=460 mg; GFR=90 mL/min; Target AUC=4 mg/mL·min

TABLE 18

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 1 x (450 mg/45 mL) + 1 x (50 mg/5 mL) OR 10 x (50 mg/5 ml) | 500 | 40 | 8.69 | 1 x (500 mg/50 mL) | 500 | 40 | 8.69 | 0 |
| 1 x (600 mg/60 mL) OR 4 x (150 mg/15 mL) | 600 | 140 | 30.4 | | | | | 21.71 |
| 2 x (450 mg/45 mL) | 900 | 440 | 95.6 | | | | | 86.91 |

*Exemplary Vials = exemplary vials of the present invention

Based on the possible vial combinations, it can be inferred that the use of vials from the present invention ensures efficient drug utilization while providing flexibility in dosing. The WREF values range from 0% to 86.91%, demonstrating that in most cases, the present invention vials significantly reduce drug wastage, particularly when replacing larger commercial vials, such as the 900 mg option, leading to an 86.9100 reduction in wastage.

Example 5.11: Dose=500 mg; GFR=90 mL/min;
Target AUC=1 mg/mL·min

TABLE 19

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 10 x (50 mg/5 mL) OR 1 x (450 mg/45 mL) + 1 x (50 mg/5 ml) | 500 | 0 | 0 | 1 x (500 mg/50 mL) | 500 mg | 0 | 0 | 0 |
| 4 x (150 mg/15 mL) OR 1 x (450 mg/45 mL) + 1 x (150 mg/15 mL) OR 1 x (600 mg/60 mL) | 600 | 100 | 20 | | | | | 20 |
| 2 x (450 mg/45 mL) | 900 | 400 | 80 | | | | | 80 |

*Exemplary Vials = exemplary vials of the present invention

Based on the possible vial combinations, it can be inferred that the use of vials from the present invention ensures efficient drug utilization while maintaining flexibility in dosing. The WREF values range from 0% to 80%, demonstrating that in most cases, the present invention vials help significantly reduce drug wastage, particularly when replacing larger commercial vials, such as the 900 mg option, leading to an 80% reduction in wastage.

Example 5.12: Dose=575 mg; GFR=90 mL/min;
Target AUC=1 mg/mL·min

TABLE 20

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 12 x (50 mg/5 mL) OR 1 x (450 mg/45 mL) + 3 x (50 mg/5 mL) OR 1 x (450 mg/45 mL) + 1 x (150 mg/15 mL) OR 1 x (450 mg/45 mL) + 1 x (150 mg/15 mL) OR 4 x (150 mg/15 mL) OR 1 x (600 mg/60 mL) | 600 | 25 | 4.3 | 1 x (500 mg/50 mL) + 1 x (80 mg/8 mL) | 580 | 5 | 0.8 | 3.5 |
| 2 x (450 mg/45 mL) | 900 | 325 | 56.5 | | | | | 55.7 |

*Exemplary Vials = exemplary vials of the present invention

Based on the possible vial combinations, it can be inferred that the use of vials from the present invention ensures efficient drug utilization while maintaining dosing flexibility. The WREF values range from 3.5% to 55.7%, demonstrating that the present invention vials significantly reduce drug wastage, particularly in cases where larger commercial vials, such as the 900 mg option, are used, leading to a 55.7% reduction in wastage.

Example 5.13: Dose=600 mg; GFR=90 mL/min; Target AUC=1 mg/mL·min

TABLE 21

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 12 x (50 mg/5 mL) OR 4 x (150 mg/15 mL) OR 1 x (450 mg/45 mL) + 3 x (50 mg/5 mL) OR 1 x (450 mg/45 mL) + 1 x (150 mg/15 mL) OR 1 x (600 mg/60 mL) | 600 | 0 | 0 | 1 x (500 mg/50 mL) + 1 x (80 mg/8 mL) + 1 x (20 mg/2 mL) | 600 | 0 | 0 | 0 |
| 2 x (450 mg/45 mL) | 900 | 300 | 50 | | | | | 55.7 |

*Exemplary Vials = exemplary vials of the present invention

The analysis of vial combinations demonstrates that the use of vials from the present invention ensures efficient drug utilization and flexibility in dosing. The WREF values range from 0% to 55.7%, highlighting a significant reduction in drug wastage in certain cases.

In cases where WREF is 0%, such as when using 600 mg of drug, the wastage remains the same as commercial vials, ensuring no additional loss while maintaining dosing efficiency. However, it is important to note that achieving this 0% wastage requires a higher number of vials, which may lead to increased handling efforts for healthcare providers. Despite this, the present invention vials provide an optimal alternative without increasing drug loss.

For higher doses, such as 900 mg, the present invention vials achieve a 55.7% reduction in wastage, demonstrating their advantage in minimizing drug loss.

Example 5.14: Dose=625 mg; GFR=90 mL/min; Target AUC=1 mg/mL·min

TABLE 22

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 13 x (50 mg/5 mL) OR 4 x (150 mg/15 mL) + 1 x (50 mg/5 mL) OR 1 x (450 mg/45 mL) + 4 x (50 mg/5 mL) OR 1 x (450 mg/45 mL) + 1 x | 650 | 25 | 4.0 | 1 x (500 mg/50 mL) + 1 x (80 mg/8 mL) 3 x (20 mg/2 mL) | 640 | 15 | 2.4 | 1.6 |

TABLE 22-continued

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| (150 mg/15 mL) + 1 x (50 mg/5 mL) | | | | | | | | |
| 5 x (150 mg/15 mL) | 750 | 125 | 20 | | | | | 17.6 |
| 2 x (450 mg/45 mL) | 900 | 275 | 44 | | | | | 41.6 |

*Exemplary Vials = exemplary vials of the present invention

The comparison between commercial vials and the present invention vials highlights a significant reduction in drug wastage while maintaining dosing flexibility. The WREF values range from 1.6% to 41.6%, indicating the improved efficiency of the present invention vials.

Example 5.15: Dose=690 mg; GFR=90 mL/min; Target AUC=1 mg/mL·min

TABLE 23

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 14 x (50 mg/5 mL) OR 4 x (150 mg/15 mL) + 2 x (50 mg/5 mL) OR 1 x (450 mg/45 mL) + 5 x (50 mg/5 mL) OR 1 x (450 mg/45 mL) + 1 x (150 mg/15 mL) + 3 x (50 mg/5 ml) | 700 | 10 | 1.4 | 1 x (500 mg/50 mL) + 2 x (80 mg/8 mL) + 2 x (20 mg/2 mL) | 700 | 10 | 1.4 | 0 |
| 5 x (150 mg/15 mL) | 750 | 60 | 8.69 | | | | | 7.29 |
| 2 x (450 mg/45 mL) | 900 | 210 | 30.4 | | | | | 29 |

*Exemplary Vials = exemplary vials of the present invention

The comparison of commercial vials with the present invention vials demonstrates a notable reduction in drug wastage while maintaining dosing efficiency. The WREF values range from 0% to 29%, emphasizing the advantages of the present invention vials in minimizing drug loss.

For a total drug quantity of 700 mg, the WREF is 0%, indicating that the wastage remains the same as commercial vials, ensuring no additional loss. However, it is important to note that in this case, the number of vials remains high, which may impact handling and administration efficiency. At higher doses, such as 750 mg, the wastage reduction reaches 7.29%. For 900 mg, the WREF is 29%, reflecting a significant decrease in wastage, making the vials of the present invention a more cost-effective and efficient choice for higher dosing needs.

Example 5.16: Dose=750 mg; GFR=90 mL/min;
Target AUC=1 mg/mL·min

TABLE 24

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 15 x (50 mg/5 mL) OR 5 x (150 mg/15 mL) OR 1 x (450 mg/45 mL) + 1 x (150 mg/15 mL) + 2 x (50 mg/5 mL) OR 1 x (450 mg/45 mL) + 1 x (150 mg/15 mL) + 3 x (50 mg/5 mL) | 750 | 0 | 0 | 1x (500 mg/50 mL) + 1 x (80 mg/8 mL) + 1 x (20 mg/2 mL) + 1 x (150 mg/15 mL) | 0 | 0 | 0 | 0 |

*Exemplary Vials = exemplary vials of the present invention

The comparison between commercial vials and the present invention vials highlights an efficient dosing strategy with minimal to no drug wastage. The WREF is 0% across all cases, indicating that the wastage remains the same between both vial types, ensuring no additional loss.

For a total drug amount of 750 mg, both commercial vials and the present invention vials demonstrate zero wastage, making them equally efficient in terms of drug utilization. However, the number of vials required in commercial options is relatively high, which may impact patient compliance and healthcare provider compliance due to increased handling and preparation time.

The use of the present invention vials allows for optimized dosing with a reduced number of vials, potentially enhancing ease of administration, patient compliance, and healthcare provider compliance. This approach ensures cost-effectiveness, convenience, and consistent dosing accuracy while maintaining wastage at zero.

Example 5.17: Dose=900 mg; GFR=90 mL/min;
Target AUC=1 mg/mL·min

TABLE 25

| Number x Strength of Commercial Vials (mg/mL) | Total Drug (mg) | Drug Waste or Carryover (mg) | % Wastage (Wc) | Number x Strength of Exemplary Vials* (mg/mL) | Total Drug (mg) | Drug Waste or Carryover (mg) | % Wastage (Wp) | WREF (%) = Wc-Wp |
|---|---|---|---|---|---|---|---|---|
| 18 x (50 mg/5 mL) OR 6 x (150 mg/15 mL) OR 4 x (150 mg/15 mL) + 6 x (50 mg/5 mL) OR 2 x (450 mg/45 mL) | | | | 1x (500 mg/50 mL) + 4 x (80 mg/8 mL) + 4 x (20 mg/2 mL) | 900 | 0 | 0 | 0 |

*Exemplary Vials = exemplary vials of the present invention

The analysis demonstrates that both commercial vials and the present invention vials effectively achieve zero drug wastage (WREF=0%), ensuring optimal drug utilization without additional loss. This indicates that the present invention vials provide equivalent efficiency in minimizing wastage compared to commercial vials.

However, in the case of commercial vials, the number of vials required is significantly high, particularly when using 18 vials of 50 mg/5 mL or a combination of 6 vials of 150 mg/15 mL. This increased vial count may affect patient compliance and healthcare provider compliance, as it leads to greater handling time, increased preparation steps, and a higher risk of administration errors.

Certain embodiments of the present invention provide injectable carboplatin formulation containing vials that offer a more streamlined approach with a reduced number of vials; and improve ease of administration, workflow efficiency, and overall convenience for both patients and healthcare providers. By maintaining zero wastage while improving dosing efficiency, this approach ensures a more practical and cost-effective solution.

The comparative analysis of commercial vials and exemplary vials of the present invention (see, e.g., Example 5), highlights significant improvements in drug utilization, patient compliance, and healthcare provider efficiency. Exemplary vials of the present invention consistently demonstrate a reduction in drug wastage, ensuring optimal resource utilization. In the cases where wastage remains the same as commercial vials, exemplary vials of the present invention still reduce the number of vials required, thereby enhancing dosing efficiency and compliance.

Moreover, commercial vial configurations often require a higher number of vials, which can increase handling time, preparation complexity, and the risk of administration errors, potentially impacting both patient and healthcare provider compliance. In contrast, some embodiments of the present invention—by offering optimized vial strengths and combinations—improve workflow efficiency, reduce operational burden, and enhance ease of administration.

What is claimed is:

1. A stable injectable carboplatin formulation, comprising:
   about 10 mg/mL of carboplatin, or a pharmaceutically acceptable derivative thereof;
   a pharmaceutically acceptable vehicle;
   wherein the formulation has a pH of from about 5 to about 7;
   wherein the formulation has a dissolved oxygen level of not less than about 28 ppm;
   wherein the formulation is filled in a glass vial selected from:
   (i) a vial having a capacity of about 5 mL and a fill volume of from about 2.15 mL to about 2.35 mL with a headspace of from about 77% to about 82%;
   (ii) a vial having a capacity of about 10 mL and a fill volume of from about 8.2 mL to about 8.8 mL with a headspace of from about 47% to about 58%; and
   (iii) a vial having a capacity of about 50 mL and a fill volume of from about 50.2 mL to about 55.3 mL with a headspace of from about 20% to about 30%; and
   wherein the headspace comprises oxygen gas in an amount effective to maintain a 1,1-cyclobutanedicarboxylic acid level of not more than 1.0%, based on the weight of carboplatin, and a total degradation impurity level at not more than 2.5%, based on the weight of carboplatin, when stored at room temperature for 24 months.

2. The formulation of claim 1, wherein the pharmaceutically acceptable vehicle comprises Water for Injection (WFI).

3. The formulation of claim 1, wherein the formulation provides a Waste Reduction Efficiency Factor (WREF) of up to about 500%.

4. The formulation of claim 1, wherein the formulation retains its stability for at least eight (8) hours after dilution with 5% D5W or 0.9% Sodium Chloride Injection, USP.

5. A method for enhancing patient and/or healthcare provider compliance with an injectable carboplatin formulation, comprising:
   (i) preparing an injectable carboplatin formulation according to claim 1;
   (ii) calculating a therapeutically effective dose of carboplatin based on body surface area (BSA), glomerular filtration rate (GFR), and/or target area under the curve (AUC);
   (iii) administering said therapeutically effective dose of carboplatin to a patient in need thereof;
   wherein said therapeutically effective dose of carboplatin is provided in from about 1 to about 15 vials; and
   wherein said injectable carboplatin formulation according to claim 1 provides a WREF up to about 500%.

6. A process for preparing a formulation according to claim 1, comprising the steps of:
   (i) admixing carboplatin, or a pharmaceutically acceptable derivative thereof, with an oxygen enriched aqueous solvent to form a solution wherein the level of dissolved oxygen in said solution is not less than 28 ppm;
   (ii) sterilizing said solution;
   (iii) filling the sterilized solution of step (ii) into a glass vial, flushing and filling the available head space with oxygen; and
   (iv) stoppering and sealing said glass vial.

7. A method for treating recurrent ovarian carcinoma, comprising:
   administering a therapeutic dose of an injectable carboplatin formulation according to claim 1 to a patient in need thereof, on day 1, every 4 weeks;
   wherein said therapeutic dose of carboplatin is 360 mg/m$^2$ IV; and
   wherein said therapeutic dose is provided by from about 1 vial to about 15 vials; and
   wherein the method provides a WREF up to about 500%.

8. The method according to claim 7, wherein the therapeutic dose is provided by from about 1 vial to about 10 vials.

9. A method for treating advanced ovarian cancer, comprising:
   administering a therapeutic dose of an injectable carboplatin formulation according to claim 1, in combination with cyclophosphamide, to a patient in need thereof, on day 1, every 4 weeks for 6 cycles;
   wherein said therapeutic does of carboplatin is 300 mg/m$^2$ IV; and
   wherein said therapeutic dose is provided using from about 1 vial to about 15 vials; and
   wherein the method provides a WREF up to about 500%.

10. The method according to claim 9, wherein the therapeutic dose is provided by from about 1 vial to about 10 vials.

* * * * *